United States Patent [19]

Schnur et al.

[11] Patent Number: 4,970,318

[45] Date of Patent: Nov. 13, 1990

[54] AROMATIC AND HETEROCYCLIC CARBOXAMIDE DERIVATIVES AS ANTINEOPLASTIC AGENTS

[75] Inventors: Rodney C. Schnur, Mystic; Anton F. J. Fliri, Norwich, both of Conn.

[73] Assignee: Pfizer Inc., New York, N.Y.

[21] Appl. No.: 336,923

[22] Filed: Apr. 12, 1989

Related U.S. Application Data

[63] Continuation-in-part of Ser. No. 198,034, May 24, 1988, abandoned.

[51] Int. Cl.$^5$ ............................................ C07D 277/82
[52] U.S. Cl. .................................... 546/198; 544/135; 544/368; 548/150; 548/163
[58] Field of Search ................ 548/163, 150; 514/367, 514/228.2, 233.5, 255, 321; 544/58.7, 135, 368; 546/198

[56] References Cited

U.S. PATENT DOCUMENTS 4,563,527  1/1986  Fujii et al. .
4,594,425  6/1986  Musser ................................. 548/161
4,732,916  3/1988  Satoh et al. .

Primary Examiner—Robert Gerstl
Attorney, Agent, or Firm—Peter C. Richardson; J. Trevor Lumb; James M. McManus

[57] ABSTRACT

Acyl derivatives of 2-aminobenzothiazole and alkylated analogs thereof as antitumor agents.

39 Claims, No Drawings

AROMATIC AND HETEROCYCLIC CARBOXAMIDE DERIVATIVES AS ANTINEOPLASTIC AGENTS

CROSS REFERENCE TO RELATED APPLICATION

This application is a continuation-in-part of application Ser. No. 198,034, filed May 24, 1988, now abandoned.

BACKGROUND OF THE INVENTION

Because cancer is second only to heart and vascular diseases as a cause of death in man, considerable effort and research has been expended in developing some form of chemotherapy to successfully treat the various kinds of human cancers. Tumors, one common manifestation of cancer in man, which are abnormal masses of new tissue growth, can bring physical discomfort and drain the body of its vital energies.

Many of the antitumor compounds recently discovered have been natural products. These include heterocyclic lactams from marine sponges (U.S. Pat. No. 4,729,996), succinimide derivatives of indole alkaloids (U.S. Pat. No. 4,667,030) and indoledione derivatives from marine sponges (U.S. Pat. No. 4,731,366). Antitumor activity has also been found in synthetic acylurea derivatives (U.S. Pat. No. 4,677,111).

U.S. Pat. No. 4,563,527 claims a series of naphthyl amidines as antitrypsin, anti-plasmin, anti-kallikrein and anti-thrombin agents.

SUMMARY OF THE INVENTION

It has now been found that compounds of the formulae I-IV

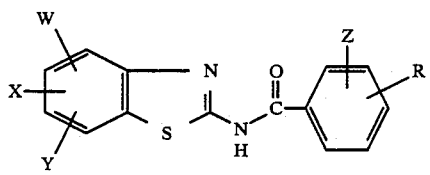

I and

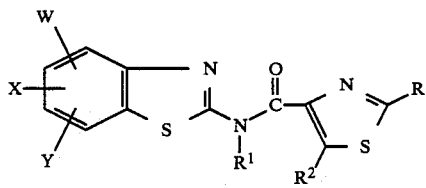

II and

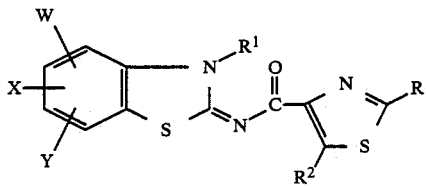

III and

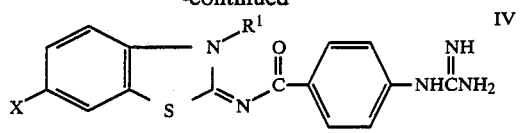

IV or a pharmaceutically acceptable salt thereof, where X is ($C_1$-$C_5$)alkyl, hydrogen, ($C_1$-$C_5$)alkoxy, ($C_1$-$C_5$)alkylthio, ($C_1$-$C_5$)alkylsulfinyl, ($C_1$-$C_5$)alkylsulfonyl, fluoro, chloro, bromo, nitro, trifluoromethyl, carbamyl, N,N-di($C_1$-$C_3$)alkylcarbamyl, phenyl, fluorophenyl, methoxyphenyl, hydroxyphenyl, cyano, cyclohexyl or hydroxy ($C_1$-$C_5$)alkyl; Y is hydrogen, ($C_1$-$C_5$)alkyl, ($C_1$-$C_5$)alkoxy, fluoro or chloro; W is hydrogen, ($C_1$-$C_5$)alkoxy, cyano, fluoro, chloro or bromo; X and Y when taken together form a benzo ring or a tetrahydrobenzo ring; Z is hydrogen, fluoro, chloro, bromo or ($C_1$-$C_3$)alkyl; R is a substituent of the formula

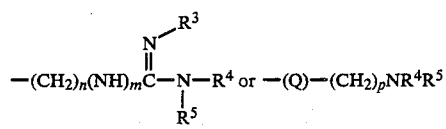

where n is an integer of 0 to 2; m is an integer of 0 to 1; $R^3$, $R^4$ and $R^5$ are each hydrogen or ($C_1$-$C_3$)alkyl; Q is $CH_2$, O, $NR^4$ or S; p is an integer of 2 to 3; $R^4$ and $R^5$ when taken together with the nitrogen to which they are attached are piperidino, pyrrolidino, morpholino, thiomorpholino, piperazino or 4-($C_1$-$C_5$)alkylpiperazino; $R^1$ is hydrogen or methyl; $R^2$ is hydrogen, ($C_1$-$C_4$)alkyl, nitro, cyano, trifluoromethyl, fluoro, chloro or bromo; and $R^6$ is ($C_1$-$C_3$)alkyl, ($C_1$-$C_3$)alkoxycarbonylmethyl, with the proviso that in compounds of formula I, R is at the m or p position to the carbonyl attachment and when Q is O, $NR^4$ or S, p is 2 to 3, are antitumor agents.

Preferred in this group of compounds are those of the formula II, where R is

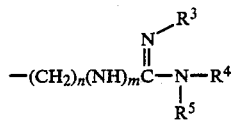

where n is 0, m is 1, $R^3$, $R^4$ and $R^5$ are each hydrogen, W is hydrogen, $R^1$ is hydrogen and $R^2$ is hydrogen, ($C_1$-$C_4$)alkyl or bromo. Especially preferred within this group are compounds where X is 6-trifluoromethyl and Y and $R^2$ are each hydrogen; where X is 5-fluoro, Y is hydrogen and $R^2$ is i-propyl; where X and Y taken together are 4,5-benzo and $R^2$ is hydrogen; where X is 4-methoxy, Y is hydrogen and $R^2$ is ethyl; where X is 5-fluoro, Y is hydrogen and $R^2$ is methyl; where X is 5-fluoro, Y is hydrogen and $R^2$ is methyl; where X is 5-fluoro, Y is 7-fluoro and $R^2$ is ethyl; where X is 4-fluoro, Y is 7-methyl and $R^2$ is ethyl; where X is 6-cyano, Y is hydrogen and $R^2$ is methyl; where X is 5-chloro, Y is 6-methyl and $R^2$ is hydrogen; where X is 7-trifluoromethyl, Y is 6-chloro and $R^2$ is hydrogen; where X is 6-phenyl, Y is 4-methoxy and $R^2$ is hydrogen; where X is 5-fluoro and Y and $R^2$ are each hydrogen; where X is 5-chloro, Y is hydrogen and $R^2$ is methyl; where X is 5-fluoro, Y is hydrogen and $R^2$ is ethyl; where X is phenyl and Y and $R^2$ is ethyl; where X is phenyl and Y and $R^2$ are each hydrogen; where X is 5-fluoro, Y is 6-fluoro and $R^2$ is hydrogen; where X is 4-methyl, Y is 5-chloro and $R^2$ is hydrogen; where X is 5-fluoro, Y is 6-bromo and $R^2$ is hydrogen; and where X is 5-fluoro, Y is hydrogen and $R^2$ is bromo.

Also preferred are compounds of formula II, where R is

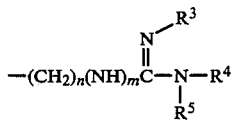

where n is 0, m is 1, $R^1$, $R^3$, $R^4$ and $R^5$ are each hydrogen and $R^2$ is $(C_1-C_4)$alkyl. Especially preferred within this group is the compound where X is 7-fluoro, Y is 6-fluoro, W is 4-methoxy and $R^2$ is ethyl.

A third preferred group of compounds are those of formula II, where R is

where p is 2, $R^4$ and $R^5$ are each hydrogen or $(C_1-C_3)$alkyl and $R^1$ and $R^2$ are each hydrogen. Especially preferred within this group are compounds where Q is S, $R^4$ and $R^5$ are each hydrogen, X is 6-phenyl and Y and W are each hydrogen; where Q is NH, $R^4$ and $R^5$ are each hydrogen, Z is 6-phenyl and Y and W are each hydrogen; where Q is S, $R^4$ and $R^5$ are each hydrogen, X is 5-fluoro and Y and W are each hydrogen; and where Q is NH, $R^4$ and $R^5$ are each methyl, X is 6-cyano and Y and W are each hydrogen.

A fourth group of preferred compounds are those of formula I, where Z is hydrogen and R is

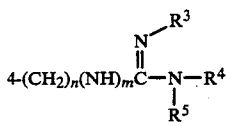

where n is 0, m is 1 and $R^3$, $R^4$ and $R^5$ are each hydrogen. Especially preferred within this group are the compounds where X is 6-nitro and Y and W are each hydrogen and where X is 5-fluoro, Y is 6-fluoro and W is hydrogen.

A fifth group of preferred compounds are those of formula I where R is

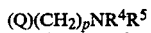

where $R^4$ and $R^5$ are hydrogen or $(C_1-C_3)$alkyl or together with the nitrogen is piperidino, $R^1$ is hydrogen, W is hydrogen and $R^2$ is hydrogen or $(C_1-C_4)$alkyl. Especially preferred within this group are the compounds where X is 5-chloro, Y is 6-chloro, $R^2$ is ethyl, Q is NH, p is 2 and $R^4$ and $R^5$ are each methyl; where X is 5-chloro, Y is 6-chloro and $R^2$ is ethyl, Q is NH, p is 3, and $R^4$ and $R^5$ are each methyl; where X is 6-cyano, Y is hydrogen, $R^2$ is ethyl, Q is NH, p is 3 and $R^4$ and $R^5$ are each methyl; where X is 6-cyano, Y is hydrogen, $R^2$ is ethyl, Q is NH, p is 2 and $R^4$ and $R^5$ together with the nitrogen is piperidino; and where X is 6-n-butyl, Y is hydrogen, $R^2$ is hydrogen, Q is $CH_2$, p is 0 and $R^4$ and $R^5$ are each hydrogen.

Also part of the present invention is a method for treating tumors in mammals which comprises administering to said mammals an antitumor effective amount of a compound selected from formulae I-IV or a pharamaceutically acceptable salt thereof.

In designating the substituents such definitions as $(C_1-C_5)$alkyl mean alkyl of one to five carbon atoms, etc.

Also considered as part of this invention are compounds of the formula

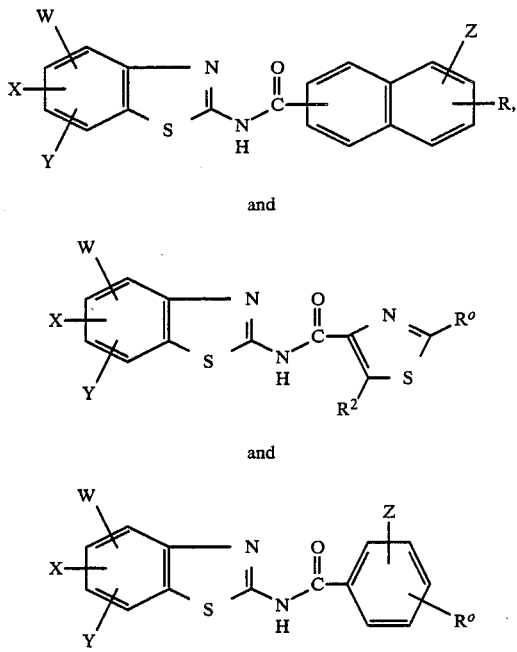

where W, X, Y, Z, R and $R^2$ are as defined herein and $R^0$ is

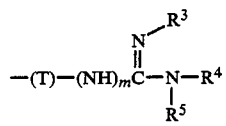

where T is $-OCH_2CH_2-$, $-SCH_2CH_2-$, $-(CH_2)_p-$ or a bond, and m, p, $R^3$, $R^4$ and $R^5$ are as defined herein.

DETAILED DESCRIPTION OF THE INVENTION

The compounds of formulae I and II are prepared by the acylation of the appropriate 2-aminobenzothiazole with a carboxy activated benzoic or thiazolyl carboxylic acid.

The activated acid can consist of an acid halide or an activated ester or mixed anhydride. The preferred acylating agent is either the N-hydroxysuccinimide ester or the acid chloride.

The coupling reaction can be achieved by contacting one mole of the appropriate benzoic or thiazolyl carboxylic acid N-hydroxysuccinimide ester hydrochloride with from 1 to 2 moles of the requisite 2-aminobenzothiazole and about 0.01 mole of hydroquinone in a reaction-inert solvent such as dimethylformamide, dimethylsulfoxide, or N-methyl-2-pyrrolidone. The reaction is heated in the dark for about 1 to 36 hours at a reaction temperature of 20-180° C.

On completion of the reaction, the reaction mixture is diluted with methanol, filtered, if necessary, and the filtrate applied to the protonated form of an ionexchange resin (pH 5-6) such as GC 50 (Aldrich Chemical Co., Inc.). The resin-product complex is then washed sufficiently with methanol, water, dimethylsulfoxide, dimethylformamide or acetonitrile or mixtures thereof, to remove all the remaining, unreacted 2-aminobenzothiazole.

The product is freed from the resin complex by treating the complex with a 0.1-0.01 molar solution of an acid such as hydrochloric acid, hydrobromic acid, methane sulfonic acid, lactic acid or acetic acid in such solvents as water, methanol or acetonitrile. The wash liquids are combined and concentrated. The product, isolated as the salt of the acid wash, precipitates as the solution is concentrated, and is collected by filtration. Further purification can be carried out by recrystallization from such solvents as dimethylformamide, tetrahydrofuran, ethyl acetate, dimethylsulfoxide, N-methyl-2-pyrrolidone or methanol or mixtures thereof.

A modification of this procedure comprises contacting one mole of the requisite acid N-hydroxysuccinimide ester, or optionally an acid addition salt, with 1.0-2.0 moles of the corresponding 2-aminobenzothiazole hydrochloride, 0.01 mole of hydroquinone and, if required, 0.01 mole of 4-dimethylaminopyridine in a reaction-inert anhydrous solvent such as dimethylformamide, dimethylsulfoxide, tetrahydrofuran, ethyl acetate, benzene, toluene, acetonitrile or N-methyl-2-pyrrolidone or mixtures thereof. The reaction time is about 1-36 hours depending on the reaction temperature, which is from about 20-180° C.

On completion of the reaction, the reaction mixture is allowed to cool to room temperature, and the precipitated solid, which is usually an acid addition salt of the desired product, is filtered. The filtrate, containing the remainder of the product, is adjusted to a pH of about 7-9 using such bases as pyridine, aqueous alkali bicarbonates, alkali carbonates or alkali hydroxides, and the product, in neutral form, isolated by filtration or extraction with a water-immiscible solvent, such as ethyl acetate, methylene chloride, chloroform or diethyl ether. The isolated product can subsequently be converted to an acid addition salt by treating a solution of the neutral product with an equivalent of an appropriate inorganic or organic acid. The originally obtained acid addition salt can be crystallized from any one of the previously mentioned recrystallizing solvents, or it can be converted to the neutral compound by adjusting an aqueous solution of the salt to a pH of 7-10 and isolating the neutral product as described above.

A second modification of the process for preparing the compounds of formulae I and II comprises, initially, containing one mole of the appropriate benzoic or thiazolyl carboxylic acid with one mole of N-, 0-bistrimethylsilyl acetamide in tetrahydrofuran at elevated temperatures until the mixture is homogeneous, followed by the addition of 2 moles of thionyl chloride. The resulting acid chloride coupling reagents may precipitate as acid addition salts.

Alternately, the acid chlorides can be prepared by heating the appropriate acids with a large excess of thionyl chloride, in an suitable solvent such as tetrahydrofuran, followed by concentration under vacuum to obtain the desired intermediate acid chloride hydrochloride salt.

The above mentioned acid chlorides are generally employed in the next coupling reaction without purification. In practice, one mole of the acid chloride hydrochloride is treated with 1.0-4.0 moles of the desired 2-aminobenzothiazole in a reaction-inert solvent such as those mentioned previously when an activated ester was employed instead of an acid chloride The reaction is carried out at room temperature with a reaction time of 1-24 hours. The completed reaction can be neutralized with ammonium hydroxide to pH 7-10 and the neutral product either filtered from the reaction or extracted with a water immiscible solvent such as previously mentioned.

The compounds of formulae I and II can also be prepared through the condensation of the benzoic or thiazolyl carboxylic acid esters and the alkali metal salt, such as the sodium salt, of the appropriate 2-aminobenzothiazole.

In practice, a solution of one mole of the requisite ester in a reaction inert solvent, such dimethylformamide, dimethylsulfoxide or acetonitrile, is added to a suspension of about one mole of the sodium salt of the desired 2-aminothiazole, also in a similar reaction-inert solvent, the sodium salt having been prepared in situ by the reaction of the 2-aminobenzothiazole with an equivalent of oil free sodium hydride.

The reaction time at ambient temperatures is about 24 hours. The reaction mixture is then diluted with water and the product precipitated by the addition of sufficient 1N hydrochloric acid to give a pH of 7. The product can be purified by conventional means such as chromatographing or recrystallization.

The formation of the compounds of formulae III and IV result from the alkylation of the compounds of formulae II and I, respectively.

In practice, the neutral compounds of formulae I and II in a reaction inert solvent such as dimethylsulfoxide, dimethylformamide or N-methyl-2-pyrrolidone are treated with about an equimolar amount of the alkylating agent, generally as halide and the reaction mixture heated at steam bath temperature until the reaction is homogeneous. The reaction mixture is cooled to room temperature resulting in the precipitation of the product as an acid addition salt, the anion of which is derived from the halide of the alkylating agent.

As previously indicated, the present invention embraces pharmaceutically acceptable salts of the biologically active compounds. Such salts are those which are non-toxic at the dosages administered. Since compounds of the invention may contain both basic and acidic groups, both acid addition and alkali addition salts are possible. Pharmaceutically acceptable acid addition salts include e.g., the hydrochloride, hydrobromide, hydroiodide, sulfate, bisulfate, phosphate, acid phosphate, acetate, lactate, maleate, mesylate, fumarate, citrate, acid citrate, tartrate, bitartrate, succinate, gluconate, glutamate, aspartate and saccharate salts. Pharmaceutically acceptable alkali addition salts include e.g., the sodium, potassium, calcium and magnesium salts. Conventional methods of forming acid addition and alkali addition salts may be employed.

The compounds of formulae III and IV are alkylated on the nitrogen containing the acidic proton removed during the formation of basic salts and, consequently, can only form acid addition salts.

The activity of the compounds of this invention as antitumor agents can be determined by several tests. One of the procedures which is accepted as a reliable test for the evaluation of antitumor agents is the Experimental Metastasis, Survival (EMS) Assay for evaluation of cancer therapeutants. This test is designed for the detection and evaluation of cancer therapeutants. It employs the Lewis lung carcinoma (3LL) which is the most frequently used tumor worldwide for the discovery of antimetastatic and antitumor agents. This tumor has been shown to be related in histopathology and chemotherapeutic responses to human lung carcinomata. The design of the system is similar to that used by the National Cancer Institute tumor screens, but employs technical modifications to provide increased reproducibility and precision. The values for compounds active in this screen can be compared to published values for anticancer drugs. The tumor was selected for its high predictivity rate for clinical success.

The test is carried out as follows:

1. Adult female (C57BL/6 ×DBA/2)F1 hybrid mice (18–20 g, n=7/group) are given an intravenous (lateral tail vein) injection of 4–6 ×10E5 log phase 3LL Lewis lung carcinoma cells on day 0, which initiates pulmonary arrest, extravasation and pulmonary metastatic tumor growth.

2. At various times after iv tumor challenge mice are treated with test agents. The standard operating procedure involves intraperitoneal administration for each of 8 consecutive days, beginning on the second day after tumor challenge (i.e., qd 2-9).

3. The mice are monitored daily, throughout the experiment, for compound-related or tumor-related deaths. The median survival time (MST in days) is used to compute the value for T/C as follows:

$$T/C\ (\%) = MST(treated)/MST(controls) \times 100\%$$

4. By this formula, compounds which have a value for T/C>124% and which are statistically significant in the Armitage-Cochran test (P<0.05) are considered active. Substantial activity is associated with values for T/C of >150%. Outstanding activity (T/C>200%) in this assay is comparable to the best of the clinically active drugs such as adriamycin and cyclophosphamide.

5. During preliminary work, it has been observed that the MST for vehicle controls ranges from 16–20 days, with 17 days occurring most frequently.

The compounds of the present invention can be administered as antitumor agents by either the oral or parental routes of administration. In general, these antitumor compounds are normally administered orally in dosages ranging from about 6 mg to about 400 mg per kg of body weight per day and 1 mg to about 200 mg per kg of body weight per day when given parenterally; variations will necessarily occur depending upon the condition of the subject being treated and the particular compound being administered. It is to be noted that these compounds may be administered in combination with pharmaceutically acceptable carriers by either of the routes previously indicated, and that such administration can be carried out in both single and multiple dosages.

The novel compounds of the invention can be orally administered in a wide variety of different dosage forms, i.e., they may be formulated with various pharmaceutically acceptable inert carriers in the form of tablets, capsules, lozenges, troches, hard candies, powders, sprays, aqueous suspensions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages.

For purposes of oral administration, tablets containing various excipients such as sodium citrate, calcium carbonate and calcium phosphate may be employed along with various disintegrants such as starch and preferably potato and tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired of oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

In addition to being antitumor agents, the compounds of this invention are also protease inhibitors and have application as anti-plasmin agents.

Plasmin, an enzyme existing in the blood, is the result of the action of plasminogen tissue activator on the proenzyme plasminogen. Plasmin plays an important role in capillary blood flow and in the dissolution of fibrin. However, when this enzyme is present in abnormal amounts it causes hemorrhagic diseases. In such cases, the use of anti-plasmin agents is extremely important. The compounds of the present possess this anti-plasmin activity, which can be readily demonstrated by the assay of H. Zimmerman, et al., Proc. Natl. Acad. Sci., 75, 750 (1978).

The compounds of the present invention can be administered as anti-plasmin agents by either the oral or parental routes of administration. In general, these anti-plasmin compounds are normally administered orally in dosages ranging from about 6 mg to about 400 mg per kg of body weight per day and 1 mg to about 200 mg per kg of body weight per day when given parenterally; variations will necessarily occur depending upon the condition of the subject being treated and the particular compound being administered. It is to be noted that these compounds may be administered in combination with pharmaceutically acceptable carriers by either of the routes previously indicated, and that such administration can be carried out in both single and multiple dosages.

As antiplasmin agents, the compounds of the present invention can be administered orally in the same form as when administered as antitumor agents, making use of tablets, capsules, lozenges, troches, powder, aqueous suspensions and the like.

The following examples illustrate the invention but are not to be construed as limiting the same.

EXAMPLE 1

4-Guanidino-N-(6-nitrobenzothiazol-2-yl)benzamide hydrochloride (I,X=6-$NO_2$; W and Y=H; Z=H; m=1; n=0, and $R^3$,$R^4$ and $R^5$=H)

To a stirred, cold (−5° C.) solution of 1.07 g. of 4-guanidinobenzoic acid hydrochloride and 740 mg. of 1-hydroxybenzotriazole in 8 ml. of dimethylformamide was added 1.12 g. of dicyclohexylcarbodiimide in one portion. After two hours at 0° C., 950 mg. of 6-nitro-2-aminobenzothiazole was added and the reaction mixture was stirred at room temperature for two hours. The mixture was filtered and the filtrate applied to 35 g. of ionexchange resin GC 50 (H+ form). The column was washed with 200 ml. of water and sufficient methane until the washliquid became colorless. Following a second water/methanol wash the product was eluted from the column using a 0.05 M hydrochloric acid in methanol solution. The fractions containing the product are combined, concentrated to dryness and recrystallized from methanol, 60 mg., m.p. 311–329° C.

EXAMPLE 2

4-Guanidino-N-(6-nitrobenzothiazol-2-yl)-benzamide hydrochloride (I,X=6-$NO_2$; W and Y=H; Z=H; n=0; m=1; and $R^3$,$R^4$ and $R^5$=H)

A solution of 44.51 g. of 4-guanidinobenzoic acid N-hydroxysuccinimide ester hydrochloride, 31.3 g. of 6-nitro-2-aminobenzothiazole and 3.13 g. of hydroquinone in 200 ml. of N-methyl-2-pyrrolidone was stirred in the dark under an inert atmosphere at 175° C. for 90 minutes. The reaction mixture was cooled to room temperature, diluted with 300 ml. of methanol and filtered. The filtrate was combined with 500 g. of GC 50 ionexchange resin (H+ form) and the pH adjusted to neutral by the addition of 10–20 ml. of pyridine. The resin was washed several times with methanol, poured into a glass column and washed with methanol until the washings were colorless. The basic material was eluted with a 0.01M solution of hydrochloric acid in methanol. The fractions containing the product were combined and concentrated in vacuo until a precipitate forms. The product was filtered and dried to give 22.5 g. of material essentially identical to that obtained in Example 1.

EXAMPLE 3

4-Guanidino-N-(6-nitrobenzothiazol-2-yl)benzamide hydrochloride (I,X=6-$NO_2$; W and Y=H; Z=H; n=0; m=1; $R^3$, $R^4$ and $R^5$=H A saturated solution of 25 g. of 4-guanidinobenzoic acid N-hydroxysuccinimide ester hydrochloride and 31.2 g. of 6-nitro-2-aminobenzothiazole in dimethylformamide was stirred at 120° C. for 72 hours. The reaction was cooled to room temperature, filtered and the solids washed with a small amount of dimethylsulfoxide and methanol. The original filtrate and washings were combined and concentrated in vacuo to 100 ml. and applied to a 55 mm diameter column filled up to 22 inches with GC 50 ionexchange resin (H+ form) packed in methanol. The column was eluted with methanol until the wash liquid was colorless. Subsequently, a 0.01M hydrochloride solution in methanol was used to elute the basic product. The pH neutral fractions are collected, concentrated under vacuum and recrystallized from methanol using a Soxhlet extractor apparatus, 5.2 g. The product was identical to that obtained in Example 1.

EXAMPLE 4

Starting with the appropriate 2-aminobenzothiazole and p-guanidinobenzoic acid ester and using the procedure of Example 2, the following compounds were prepared.

| X | Y | W | m.p., °C. |
|---|---|---|---|
| 6-Cl | H | H | 315–318 dec. |
| 6-$OCH_3$ | H | H | >300 dec. |
| 6-$OC_2H_5$ | H | H | 260–263 |
| 5-$CH_3$ | 6-$CH_3$ | H | 323–325 |
| 6-$CH_3$ | H | H | 299–302 |
| H | H | H | 250–253 |
| 4-$OCH_3$ | H | H | 295–300 dec. |
| 6-Br | H | H | 289–294 dec. |
| 6-$CONH_2$ | H | H | 316–318 |
| 6-$CF_3$ | H | H | 310–312 |
| 6-$NO_2$ | 4-$CH_3O$ | H | >350 dec. |
| 6-$SCH_3$ | H | H | 270–271 |
| 6-$SO_2NH_2$ | H | H | 225–227 |
| 6-$NH_2$ | H | H | 301–302 dec. |
| 6-$SO_2CH_3$ | H | H | 301–306 dec. |
| 6-$CH(CH_3)_2$ | H | H | 283–284 |
| 6-CN | H | H | 322–326 dec. |
| 5-$CON(CH_3)_2$ | H | H | 203–205 |
| 6-$C_6H_5$ | H | H | 287–293 dec. |
| 6-$(CH_2)_3CH_3$ | H | H | 254–258 dec. |
| 6-$SOCH_3$ | H | H | 210–212 |
| 4-$CF_3$ | H | H | 265–267 |
| 4-$CH_3$ | H | H | 178 |
| 6-$(CH_2)_2OH$ | H | H | 300 dec. |
| 4-$OCH_3$ | 7-Cl | H | 314 |
| 4-$NO_2$ | H | H | 263–264 |
| 5-F | H | H | 283–284 |
| 5-F | 6-F | H | 283–284 |

EXAMPLE 5

4-Guanidino-N-(3-benzyloxycarbonylmethyl-6-nitrobenzothiazol-2-yl) benzamide hydrobromide (IV, X=6—$NO_2$; and $R^6$=$OOCCH_2$—)

A solution of 3.0 g. of 4-guanidino-N-(6-nitro-benzothiazol-2-yl)benzamide hydrochloride in 5 ml. of hot dimethylsulfoxide was treated with 25 ml. of concentrated ammonium hydroxide and 25 ml. of water. The yellow precipitate was filtered, washed successively with water (10 ml.), methanol (20 ml.), ethanol (20 ml.) and ether (20 ml.) and dried, 2.5 g.

A suspension of the above neutral compound (480 mg.) in 10 ml. of N-methyl-2-pyrrolidone and 4 g. of benzyl bromoacetate was heated at 100° C. until the reaction mixture was homogeneous. The mixture was cooled to room temperature, diluted with ethyl acetate until cloudy and allowed to stand for several hours. The solid was filtered and recrystallized from methanol, 400 mg., m.p. 242–247° C. dec.

In a similar manner was prepared from t-butyl bromoacetate 4- guanidino-N-(3-t-butoxycarbonylmethyl-6-nitrobenzothiazol-2-yl)benzamide hydrobromide, m.p. 269–275° C. dec.

EXAMPLE 6

4-Guanidinomethyl-N-(6-nitrobenzothiazol-2-yl)benzamide methanesulfonate(I, X=6—$NO_2$; W and Y=H; m=1; Z=H; n=1; $R^3$, $R^4$ and $R^5$=H)

A solution of 7.0 g. of 4-guanidinomethylbenzoic acid N-hydroxysuccinimide ester, 5.5 g. of 6-nitro-2-aminobenzothiazole and 700 mg. of hydroquinone in 60 ml. of N-methyl-2-pyrrolidone was stirred at 180° C. in the dark under an inert atmosphere for 40 minutes. The reaction mixture was cooled to room temperature, diluted with 400 ml. of methanol and allowed to stir for 30 minutes. The solids were filtered and the filtrate concentrated to 100 ml. in vacuo and applied to a column containing GC 50 (H+ form) ionexchange resin. The resin was washed with methanol until the washings were colorless. The column material was then eluted with an 0.01M solution of methanesulfonic acid in methanol. The fractions containing the product were combined, concentrated in vacuo and the residue recrystallized from methanol using a Soxhlet extractor, 1.8 g., m.p. 300° C.

EXAMPLE 7

Using the procedure of Example 6 and starting with the requisite reagents, the following compounds were prepared:

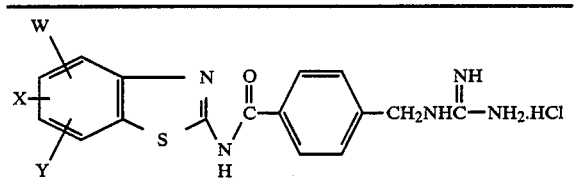

| X | Y | W | m.p., °C. |
|---|---|---|---|
| 6-$NO_2$ | H | H | 318–319 dec. |
| 6-$NO_2$ | 4-$CH_3O$ | H | 283–289 dec. |
| 6-$CF_3$ | H | H | 219–221 |
| 6-$CONH_2$ | H | H | 193–195 |

EXAMPLE 8

3-Guanidinomethyl-N-(6-phenylbenzothiazol-2-yl)benzamide hydrochloride (I, X=6—$C_6H_5$; W and Y=H; Z=H; n=1; m=1; $R^3$, $R^4$ and $R^5$=H)

A suspension of 5 g. of 3-guanidinomethylbenzoic acid N-hydroxysuccinimide ester hydrochloride, 8.8 g. of 2-amino-6-phenylbenzothiazole and 500 mg. of hydroquinone in 15 ml. of N-methyl-2-pyrrolidone was stirred at 130° C. in the dark under an inert atmosphere for 6 hours. The reaction was cooled, diluted with 200 ml. of methanol, added to 250 g. of GC 50 ionexchange resin (H+ form) and the pH adjusted to 5 with pyridine. The resin was washed with methanol until the wash liquid was colorless. The basic product was eluted with a solution of 0.01N hydrochloric acid in methanol. The fractions containing the product were combined and concentrated under vacuum. The residual product was recrystallized from methanol, 2.2 g., m.p. 180° C.

In a similar manner was prepared 3-guanidinomethyl-N-(6-nitrobenzothiazol-2-yl)benzamide hydrochloride, m.p. 295–300° C. dec.

EXAMPLE 9

2-Guanidino-N-(5-fluorobenzothiazol-2-yl)-thiazole-4-carboxamide (II, X=5—F; W and Y=H; $R^1$=H; $R^2$=H; n=0; m=1; $R^3$, $R^4$, and $R^5$=H)

A suspension of 42.86 g. of 2-amino-5-fluorobenzothiazole hydrochloride, 66.95 g. of 2-guanidinothiazole-4-carboxylic acid N-hydroxysuccinimide ester hydrochloride and 100 mg. of hydroquinone in 300 ml. of N-methyl-2-pyrrolidone was heated in the dark with stirring and under an inert atmosphere at 125° C. for 6 hours. The reaction mixture was cooled to room temperature and diluted with 500 ml. of a 5% aqueous sodium bicarbonate solution. The resulting precipitate was filtered, washed with water (3×500 ml.) and dried. The crude product was recrystallized twice from pyridine, 22.5 g., m.p. 290–291° C.

In a similar manner was prepared 2-guanidino-N-(5-chloro-6-methylbenzothiazol-2-yl)thiazole-4-carboxamide, m.p. 286–287° C. dec.

EXAMPLE 10

2-Guanidino-N-(5-fluorobenzothiazol-2-yl)-thiazole-4-carboxamide hydrochloride (II, X=5—F; W and Y=H; $R^1$=H; $R^2$=H; n=0; m=1; $R^3$, $R^4$ and $R^5$=H)

The procedure of Example 9 was repeated using 4.08 g. of 2-amino-5-fluorobenzothiazole hydrochloride, 6.37 g. of 2-guanidinothiazole-4-carboxylic acid N-hydroxysuccinimide ester hydrochloride and 10 mg. of hydroquinone in 30 ml. of N-methyl-2-pyrrolidone. After the reaction was cooled, the reaction mixture was diluted with 1.5 l. of ether causing the separation of an oily precipitate. The ether was decanted and the residual oil dissolved in 100 ml. of dimethylsulfoxide and 50 ml. of methanol. The resulting solution was added slowly to 2.5 l. of ether with stirring. The resulting precipitate was filtered and dried, 6.7 g. A sample was purified by trituration with methanol, m.p. 279–280° C.

EXAMPLE 11

2-Guanidino-N-(5-fluorobenzothiazol-2-yl)thiazole-4-carboxamide sodium salt (II, X=5—F; W and Y=H; $R^1$=H; $R^2$=H; n=0; m=1; $R^3$, $R^4$ and $R^5$=H)

A solution of 3.36 g. of the product of Example 9 in 35 ml. of dimethylsulfoxide was treated with 540 mg. of sodium methoxide in 5 ml. of methanol. After stirring for ten minutes the solution was diluted with diethyl ether until a precipitate started to form. After stirring for 30 minutes the solids were filtered, washed with a small amount of water, then ethanol and diethyl ether, and dried, m.p. 260–262° C.

A similar formation of the sodium salt from the product of Example 10 was carried out using two equivalents of sodium methoxide per mole of hydrochloride.

EXAMPLE 12

Employing the procedure of Example 10, and starting with the appropriate reagents, the following compounds were prepared as their indicated acid addition salt.

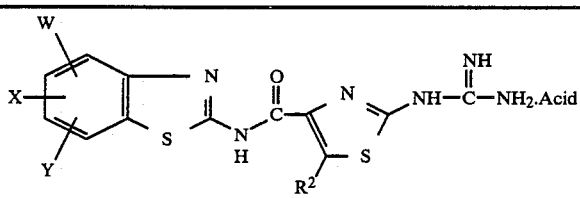

| X | Y | W | R² | m.p., °C. | Acid |
|---|---|---|---|---|---|
| 6-$CF_3$ | H | H | H | 310 dec. | HCl |
| 6-$NO_2$ | H | H | H | 295 dec. | HCl |
| 4-$CH_3O$ | H | H | H | 295 dec. | HCl |
| 6-Cl | H | H | H | 295 dec. | HCl |
| H | H | H | H | 285 dec. | HCl |
| 6-F | H | H | H | 285 dec. | HCl |
| 6-$CH_3O$ | H | H | H | 284–286 | HCl |
| 6-CN | H | H | H | 309–310 | HCl |
| 4-$CH_3$ | H | H | H | 245 dec. | HBr |
| 4-$CF_3$ | H | H | H | 272–274 | HCl |
| 6-$C_2H_5$ | H | H | H | 325–326 | HCl |
| 5-$CH_3S$ | H | H | H | 214–216 | HCl |
| 6-$NO_2$ | 4-$CH_3O$ | H | H | 289–291 | HCl |
| 5-$CH_3O$ | H | H | H | 217–218 | HCl |
| 6-$C_6H_5$ | H | H | H | 321–323 | HCl |
| 6-$CH_3(CH_2)_3O$ | H | H | H | 308–310 | HCl |
| 4-$CH_3$ | 6-$CH_3$ | H | H | 299–301 | HCl |
| 5-$CH_3$ | 6-$CH_3$ | H | H | 289–290 | HCl |
| 5-$NO_2$ | H | H | H | >350 | HCl |
| 4-$(CH_3)_2CH$ | H | H | H | 204–206 | HCl |
| 4-$CH_3S$ | H | H | H | 184–185 | HCl |
| 6-CN | 4-$C_2H_5$ | H | H | 294–297 | HCl |
| 5-$C_6H_5$ | H | H | H | 264–265 | HCl |
| 5-$CH_3(CH_2)_3O$ | H | H | H | 236–239 | HCl |
| 5-$(CH_3)_2CHO$ | H | H | H | 235 | HCl |
| 7-$C_6H_5$ | H | H | H | 333–335 | HCl |
| 6-$CH_3(CH_2)_4S$ | H | H | H | 305–307 | HCl |
| 6-$HO(CH_2)_2$ | H | H | H | 290–291 | HCl |
| 4-$CH_3$ | 5-$CH_3O$ | H | H | 284–285 | HCl |
| 4-$CH_3$ | 5-Cl | H | H | 280–283 | HCl |
| 6,7-CH=CH—CH=CH— | | H | H | 265–268 | HCl |
| 6-p-$FC_6H_4$ | H | H | H | 330 | HCl |
| 4-$CH_3$ | 7-F | H | H | 312–315 | HCl |
| 6-$CH_3$ | 7-F | H | H | 329–330 | HCl |
| 7-$NO_2$ | H | H | H | 300–303 | HCl |
| 5-$C_2H_5O$ | H | H | H | 185–188 | HCl |
| 4-$CH_3$ | 5-F | H | H | 285–288 | HCl |
| 6-$(CH_3)_3C$ | H | H | H | 320–322 | HCl |
| 4-F | 6-F | H | H | 297–299 | HCl |
| 6-$CH_3(CH_2)_2$ | H | H | H | 307 | HCl |
| 4-$CH_3$ | 6-$CH_3O$ | H | H | 292–294 | HCl |
| 4-$NO_2$ | H | H | $CH_3$ | 340 dec. | HCl |
| 6-CN | H | H | $CH_3$ | 353 | $CH_3SO_3H$ |
| 4-$CH_3O$ | H | H | $CH_3$ | 314–315 dec. | HCl |
| 5-F | H | H | $CH_3$ | 320–375 dec. | HCl |
| 5-$CH_3O$ | H | H | $CH_3$ | 299–301 dec. | HCl |
| 5-$NO_2$ | H | H | $CH_3$ | >350 dec. | HCl |
| H | H | H | $CH_3$ | 320–325 dec. | HCl |
| 6-$CH_3$ | H | H | $CH_3$ | >340 | HCl |
| 6-$C_6H_5$ | H | H | $CH_3$ | 329–333 | HCl |
| 6-F | H | H | $CH_3$ | 320–322 dec. | HCl |
| 4-$CH_3$ | H | H | $CH_3$ | 310–312 dec. | HCl |
| 4-$CH_3$ | 6-$CH_3$ | H | $CH_3$ | 344–346 dec. | HCl |
| 6-$HO(CH_2)_2$ | H | H | $C_2H_5$ | 309 dec. | HCl |
| 6-CN | H | H | $C_2H_5$ | 305–306 | HCl |
| 5-F | H | H | $C_2H_5$ | 310 | $CH_3SO_3H$ |
| 5-$CH_3O$ | H | H | $C_2H_5$ | 301 | $CH_3SO_3H$ |
| 4-$CH_3O$ | H | H | $C_2H_5$ | 283–284 | HCl |
| H | H | H | $C_2H_5$ | 320 | HCl |
| 5-$NO_2$ | H | H | $C_2H_5$ | 317 | HCl |
| 6-F | H | H | $C_2H_5$ | 305 | HCl |
| 4-$CH_3$ | 6-$CH_3$ | H | $C_2H_5$ | 324 | HCl |
| 6-$CH_3$ | H | H | $C_2H_5$ | 320 | HCl |
| 5-F | 7-F | H | $C_2H_5$ | 298 | HCl |
| 4-F | 7-$CH_3$ | H | $C_2H_5$ | 295 | HCl |
| 4-F | H | H | $C_2H_5$ | 294–296 | $CH_2SO_3H$ |
| 6-$SO_2NH_2$ | H | H | n-$C_3H_7$ | 233–235 | HCl |
| 6-$CONH_2$ | H | H | n-$C_3H_7$ | 233–237 | HCl |
| 5-F | H | H | n-$C_3H_7$ | 276–278 | HCl |
| 6-$(CH_2)_2OH$ | H | H | n-$C_3H_7$ | 191–193 | HCl |
| 5-F | 7-F | H | n-$C_3H_7$ | 297–299 | HCl |

-continued

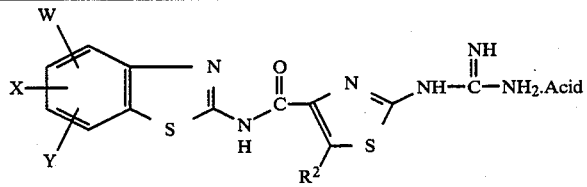

| X | Y | W | R² | m.p., °C. | Acid |
|---|---|---|---|---|---|
| 7-F | 5-F | 4-CH₃O | C₂H₅ | 266–268 | freebase |
| 5-CH₃O | H | H | n-C₃H₇ | 240–245 dec. | HCl |
| 6-CN | H | H | n-C₃H₇ | 268–271 dec. | HCl |
| 4-CH₃O | 7-Cl | H | n-C₃H₇ | 262–264 dec. | HCl |
| 6-C₆H₅ | H | H | n-C₃H₇ | 247–249 dec. | HCl |
| 4-CH₃O | H | H | n-C₃H₇ | 245–247 | HCl |
| H | H | H | n-C₃H₇ | 262–265 | HCl |
| 6-CF₃ | H | H | i-C₃H₇ | 264–284 | CH₃SO₃H |
| 6-NO₂ | H | H | i-C₃H₇ | 293–294 | CH₃SO₃H |
| 6-(CH₂)₂OH | H | H | i-C₃H₇ | 261–262 | CH₃SO₃H |
| 6-CONH₂ | H | H | i-C₃H₇ | 189–190 | CH₃SO₃H |
| 5-CH₃O | H | H | i-C₃H₇ | 281 | CH₃SO₃H |
| 5-N(CH₃)₂ | H | H | i-C₃H₇ | 172 | CH₃SO₃H |
| 6-C₆H₅ | H | H | i-C₃H₇ | 300–302 | CH₃SO₃H |
| 4-CH₃O | H | H | i-C₃H₇ | 248 | CH₃SO₃H |
| 4-CH₃O | 7-Cl | H | i-C₃H₇ | 243–244 | CH₃SO₃H |
| 5-F | H | H | i-C₃H₇ | 276–277 | CH₃SO₃H |
| H | H | H | i-C₃H₇ | 248–250 | HCl |
| 4-CH₃ | 6-CH₃ | H | i-C₃H₇ | 306–307 | HCl |
| 6-CH₃ | H | H | i-C₃H₇ | 320 | HCl |
| 6-F | H | H | i-C₃H₇ | 204 | HCl |
| 7-CF₃ | 6-Cl | H | H | 339–340 dec. | HCl |

EXAMPLE 13

Employing the procedure of Example 11, and starting with the appropriate starting materials, the sodium salt of the following compounds were prepared:

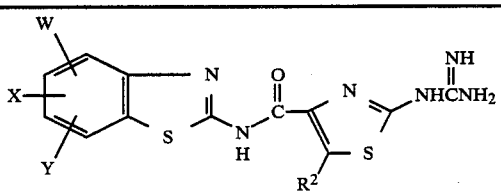

| X | Y | W | R² | m.p., °C. |
|---|---|---|---|---|
| 6-CF₃ | H | H | H | |
| 6-F | H | H | H | 290 dec. |
| 6-CH₃O | H | H | H | 259–261 |
| 4-Cl | H | H | H | 285 dec. |
| 6-CONH₂ | H | H | H | 265 dec. |
| 6-CH₃CH₂O | H | H | H | 259–260 |
| 6-CH₃ | H | H | H | 260 dec. |
| 6-(CH₃)₂CH | H | H | H | 240–242 |
| 5-CH₃O | 6-CH₃O | H | H | 230 dec. |
| 4-NO₂ | H | H | H | 234–236 |
| 6-CH₃s | H | H | H | 238–240 |
| 5-Cl | H | H | H | 248 |
| 7-CF₃ | H | H | H | 255–258 |
| 5-F | H | H | H | 275 dec. |
| 5-CF₃ | H | H | H | 205–209 |
| 4-CH₃O | 7-Cl | H | H | 228–230 |
| 5-CH₃SO₂ | H | H | H | 258–260 |
| 4-F | H | H | H | 298–300 |
| 6-CH₃(CH₂)₄SO₂ | H | H | H | 265–267 |
| 4-CH₃CH₂ | 7-F | H | H | 179–182 |
| 4-CH₃O | 7-F | H | H | 272 dec. |
| 4-CH₃CH₂ | 7-Cl | H | H | 273–275 |
| 5-CH₃O | 7-CF₃ | H | H | |
| 4-CH₃ | 6-F | H | H | 271–273 |
| 4-F | 7-F | H | H | 340 dec. |

EXAMPLE 14

Using the procedure of Example 9 and starting with the requisite reagents, the following compounds were synthesized:

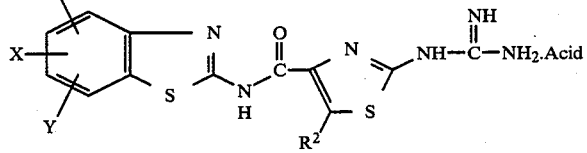

| X | Y | W | R² | m.p., °C. |
|---|---|---|---|---|
| 6-CF₃ | H | H | H | 265 dec. |
| 6-CH₃O | H | H | H | 253–254 |
| 5-F | H | H | H | 290–291 |
| 4-CH₃ | 6-CF₃ | H | H | 249 |
| 4-CH₃O | 7-CF₃ | H | H | 265–266 |
| 6-CH₃(CH₂)₅ | H | H | H | 174–175 |
| 6-NO₂ | H | H | CH₃ | 320 dec. |
| 6-CF₃ | H | H | CH₃ | 295–296 |
| 6-CN | H | H | CH₃ | 332 dec. |
| 6-(CH₂)₂OH | H | H | CH₃ | 279–280 |
| 6-CF₃ | H | H | C₂H₅ | 271–272 |
| 6-NO₂ | H | H | C₂H₅ | 297–298 |
| 5-F | H | H | C₂H₅ | 274 |
| 6-CF₃ | H | H | n-C₃H₇ | 232–233 |
| 6-NO₂ | H | H | n-C₃H₇ | 272–273 |
| 5-CH₃O | H | H | i-C₃H₇ | 297 |
| 5-N(CH₃)₂ | H | H | i-C₃H₇ | 272 |
| 6-C₆H₅ | H | H | i-C₃H₇ | 266–267 |
| 4-CH₃O | H | H | i-C₃H₇ | 266–267 |
| 6-C₆H₅ | 4-CH₃O | H | C₂H₅ | 264–265 |

EXAMPLE 15

2-Guanidino-N-(3-methyl-6-nitrobenzothiazol-2-yl) thiazole-4-carboxamide (III, X=6—NO$_2$; W and Y =H; R$^1$=CH$_3$; R$^2$=H; n=0; m=1; R$^3$, R$^4$ and R$^5$ =H) and 2-guanidino-N-methyl-N-(6-nitrobenzothiazol-2-yl)thiazole4-carboxamide (II, X=6—NO$_2$; W and Y=H; R$^1$=CH$_3$; R$^2$=H; n=0; m=1; R$^3$, R$^4$ and R$^5$=H To a solution of 2.0 g. of the sodium salt of 2-guanidino-N-(6-nitrobenzothiazol-2-yl)thiazole-4carboxamide in 20 ml. of N-methyl-2-pyrrolidone was added 739 mg. of methyl iodide. After stirring for 72 hours, the mixture was poured into 100 ml. of diethyl ether and filtered. The solids were triturated with 75 ml. of dimethylsulfoxide to give 1.01 g. of the compound related to III, m.p. 350° C. dec. The triturate was diluted with methanol and the product precipitated with diethyl ether, yielding the isomer related to II, 215 mg., m.p. 272-274° C.

EXAMPLE 16

2-(Aminoethylthio)-N-(6-phenylbenzothiazol-2-yl)-thiazole-4-carboxamide hydrochloride (II, X=6-phenyl; Y, W, R$^1$ and R$^2$=H; Q=5; p=2 and R$^4$ and R$^5$=H)

A.

2-(t-butoxycarbonylaminoethylthio)-N-(6-phenyl-benzothiazol-2-yl) thiazole-4-carboxamide A stirred suspension of 3.8 g. of (2-(t-butoxy-carbonylaminoethylthio) thiazole-4-carboxylic acid N-hydroxysuccinimide ester, 2.36 g. of 2-amino-6-phenylbenzothiazole and 200 mg. of 4-dimethylaminopyridine in 60 ml. of ethyl acetate was heated to reflux for 15 hours. The reaction mixture was cooled and concentrated to 10 ml. The precipitated product was filtered and recrystallized from ethyl acetate, 2.04 g., m.p. 171-173° C.

In a similar manner were prepared: 2-(t-butoxy-carbonylaminoethylthio) -N-(5-fluorobenzothiazol-2-yl) -thiazole-4-carboxamide, m.p. 198-199° C. and 2-(t-butoxy-carbonylaminoethylthio)-N-(3-methyl-5-fluorobenzothiazol-2-yl) thiazole-4-carboxamide, m.p. 204-205° C.

B.

2-(aminoethylthio)-N-(6-phenylbenzothiazol-2-yl)-thiazole-4-carboxamide hydrochloride A suspension of 2.04 g. of the product of Example 16A in 8 ml. of trifluoroacetic acid was stirred at room temperature overnight. The solvent was removed in vacuo and the residue suspended in 300 ml. of ethyl acetate. The suspension was washed successively with 5% sodium bicarbonate solution (3×100 ml.), water (2×100 ml.) and a brine solution (100 ml.). The organic layer was dried over sodium sulfate and concentrated to dryness. The residue was dissolved in a small amount of 0.1N methanolic hydrochloric acid and the precipitated solid filtered and dried, 840 mg., m.p. 266-267° C.

In a similar manner were prepared: 2-(aminoethylthio)-N-(5-fluorobenzothiol-2-yl) thiazole-4-carboxamide hydrochloride, m.p. 261-263° C. dec. and 2-(aminoethylthio)-N-(3-methyl-5-fluorobenzothiazol-2-yl)thiazole-4-carboxamide hydrochloride, m.p. 276-277° C. dec.

EXAMPLE 17

2-(Dimethylaminoethylamino)-N-(6-cyanobenzothiazol-2-yl) thiazole-4-carboxamide (II, X=6—CN; Y and W=H; R$^1$ and R$^2$=H; Q=NH; p=2; and R$^4$ and R$^5$=CH$_3$)

To a suspension of 288 mg. of oil free sodium hydride in 20 ml. of dry dimethylformamide was added 2.19 g. of 2-amino-6-cyanobenzothiazole. After stirring for 40 minutes, 1.52 g. of ethyl 2-(dimethylaminoethylamino)-thiazole-4-carboxylate was added in 3 ml. of dry dimethylformamide and the reaction mixture allowed to stir for 24 hours. The reaction mixture was diluted with water (200 ml.) and extracted with diethyl ether (3×250 ml.). The aqueous layer was adjusted to pH 7 with 1N hydrochloric acid and the precipitated product filtered. The solids were dissolved in 30% methanol-chloroform, dried over potassium carbonate and concentrated to dryness, 2.56 g. The crude product was chromatographed on 300 g. of silica gel using 5% methanol-chloroform and 240 tubes. Tubes 148-240 were combined and concentrated to give 510 mg. of the desired product, m.p. 201-203° C.

EXAMPLE 18

2-(Dimethylaminoethylamino)-N-(6-phenylbenzothiazol-2-yl) thiazole-4-carboxamide (II, X=6—0; Y and W; R$^1$ and R$^2$=H; Q=NH; p=2; and R$^4$ and R$^5$=CH$_3$)

Following the general procedure of Example 17, 5.58 g. of 2-amino-6-phenylbenzothiazole, 3.0 g. of ethyl 2-(dimethylaminoethylamino)thiazole-4-carboxylate and 592 mg. of oil free sodium hydride gave 2.89 g. of product after chromatographing. This material was further purified by recrystallization from acetonitrile, 2.22 g., m.p. 172-174° C.

EXAMPLE 19

2-(Dimethylaminoethylamino)-5-ethyl-N-(5,6-dichlorobenzothiazol-2-yl) thiazole-4-carboxamide (II, X=6—Cl; Y—5—Cl; W=H; R$^1$=H; R$^2$=C$_2$H$_5$; Q=NH; p=2; and R$^4$ and R$^5$=CH$_3$ Following the general procedure of Example 17, 894 mg. of 2-amino-5,6-dichlorobenzothiazole, 1.07 g. of ethyl 2-(dimethylaminoethylamino)-5-ethylthiazole-4-carboxylate and 108 mg. of oil free sodium hydride in 25 ml. of dry tetrahydrofuran were refluxed for 16 hours to give, after chromatographing on silica gel, 460 mg. of the desired product, m.p. 199-201° C.

EXAMPLE 20

2-(Dimethylaminopropylamino)-5-ethyl-N-(5,6-dichlorobenzothiazol-2-yl) thiazole-4-carboxamide (II, X=6—Cl; Y—5—Cl; W=H; R$^1$=H; R$^2$=C$_2$H$_5$; Q=NH; p=3; and R$^4$ and R$^5$=CH$_3$ In a manner similar to Example 19, 1.10 g. of 2-amino-5,6-dichlorobenzothiazole, 1.43 g. of 2-(dimethylaminopropylamino)-5-ethylthiazole-4-carboxylate and 144 mg. of oil free sodium hydride in 30 ml. of dry tetrahydrofuran gave 1.05 g. of product, m.p. 189-191° C.

EXAMPLE 21

(Dimethylaminopropylamino)-5-ethyl-N-(6-cyanobenzothiazol-2-yl) thiazole-4-carboxamide (II, X=6—CN; Y—H; W=H; $R^1$=H; $R^2$=$C_2H_5$; Q=NH; p=3; and $R^4$ and $R^5$=$CH_3$ In a manner similar to Example 17, 673 mg. of oil free sodium hydride, 4.91 g. of 2-amino-6-cyanobenzothiazole and 4.0 g. of ethyl 2-(dimethylaminopropylamino)-5-ethylthiazole-4-carboxylate in 65 ml. of dry dimethylformamide gave, after reacting at room temperature for 48 hours, 1.10 g. of product, m.p. 159–161° C.

EXAMPLE 22

2-(Piperidinoethylamino)-N-(6-cyano-benzothiazol-2-yl) thiazole-4-carboxamide II, X=6—CN; Y—H; W=H; $R^1$=H; $R^2$=H; Q=NH; p=2; and $R^4$, $R^5$=—$(CH_2)_5$—)

Using the procedure of Example 17, 678 mg. of oil free sodium hydride, 4.95 g. of 2-amino-6-cyanobenzothiazole and 4.0 g. of ethyl 2-(piperidinoethylamino)-thiazole-4-carboxylate in 65 ml. of dry dimethylformamide gave 2.0 g. of product, m.p. 230–232° C.

EXAMPLE 23

2-Aminomethyl-N-(6-n-butylbenzothiazol-2-yl)thiazole-4-carboxamide hydrobromide (II, X=n—$C_4H_9$; Y=H; W=H; $R^1$=H; $R^2$=H; Q=$CH_2$; p=0; and $R^4$ and $R^5$=H)

A. N-(4-ethoxycarbonylthiazol-2-yl)benzamide

A solution of 19.02 g. of benzoylthiourea and 19.12 g. of ethyl bromopyruvate in 300 ml. of ethanol was refluxed for 2 hours. The solvent was removed in vacuo and the residue partitioned between ethyl acetate (1 liter) and 20% aqueous sodium carbonate (400 ml.). The organic layer was separated, washed successively with 20% aqueous sodium carbonate (3×400 ml.), water (2×400 ml.) and a brine solution (2×400 ml.) and dried over sodium sulfate. The solution was concentrated to about 50 ml. and the precipitated solids filtered and dried, 20.16 g., m.p. 146–147° C.

B. 2-aminoethylthiazole-4-carboxylic acid hydrochloride

The product of Example 23A (19.16 g.) was added to 25 ml. of concentrated hydrochloric acid and refluxed for 2 hours. The reaction mixture was cooled and the product filtered and dried, 11.8 g. m.p. 281–282° C.

C. 2-(t-butoxycarbonylaminomethyl)-thiazole-4-carboxylic acid

To a cooled (10° C.) solution of 2.5 g. of the product of Example 23B in 25 ml. of dioxane was added 10 ml. of 3N aqueous sodium hydroxide solution and the solution stirred for 30 minutes at 10° C. t-Butoxycarbonic acid anhydride (3.27 g.) was added to the reaction mixture, which was then stirred for 6 hours. The mixture was allowed to warm to room temperature and the solvent removed in vacuo. The residue was dissolved in 200 ml. of water which was then extracted with ethyl acetate (4×400 ml.). The organic layer was discarded and the aqueous acidified to pH 2 with citric acid. The aqueous was extracted with ethyl acetate (4×300 ml.) and the extracts combined and extracted with water (2×100 ml.) and a brine solution (1×150 ml.). The ethyl acetate was dried over sodium sulfate and concentrated to 25 ml. The product was filtered and dried, 2.9 g., m.p. 185° C.

D. succinimido 2-(t-butoxycarbonylamino-methyl)thiazole-4-carboxylate

To a solution of 1.75 g. of the product of Example 23C in 10 ml. of tetrahydrofuran was added 940 mg. of N-hydroxysuccinimide and the solution cooled to <10° C. in an ice bath. Dicyclohexylcarbodiimide (1.67 g.) was added to the reaction mixture, which was then stirred for 16 hours under nitrogen. The solids were filtered and the solvent removed in vacuo. The residue was taken up in 800 ml. of ethyl acetate and washed with 10% aqueous citric acid solution (3×150 ml.), a saturated aqueous sodium bicarbonate solution (3×150 ml.), water (1×100 ml.) and a brine solution (1×100 ml.). The organic phase was dried over sodium sulfate and concentrated to 25 ml. The product was filtered and recrystallized from ethyl acetate, 2.12 g., m.p. 171° C.

E. 2-(t-butoxycarbonylaminomethyl)-N-(6-n-butyl-benzothiazol-2-yl) thiazole-4-carboxamide A mixture of 4.82 g. of 2-amino-6-n-butylbenzothiazole, 7.1 g. of the product of Example 23D and 250 mg. of 4-dimethylaminopyridine in 75 ml. of ethyl acetate was refluxed for 15 hours. The mixture was cooled to room temperature and diluted with 1 liter of ethyl acetate. The organic solution was washed with 10% citric acid aqueous solution (3×200 ml.), water (1×200 ml.), saturated aqueous sodium bicarbonate solution (3×200 ml.), water (1×200 ml.) and a brine solution (1×200 ml.). The organic phase was dried over sodium sulfate and concentrated to 30 ml. On cooling solids formed which were filtered and dried, 6.1 g., m.p. 143–144° C.

F. 2-aminomethyl-N-(6-n-butylbenzothiazol-2-yl)-thiazole-4-carboxamide hydrobromide A mixture of 3.5 g. of the product of Example 23E in 50 ml. of a 33% hydrogen bromide in acetic acid was heated to reflux for 10 minutes. After stirring at room temperature overnight, the reaction was diluted with 25 ml. of acetic acid and filtered. The solids were recrystallized from methanol, 723 mg., m.p. 255–257° C. dec.

We claim:

1. A compound of the formula

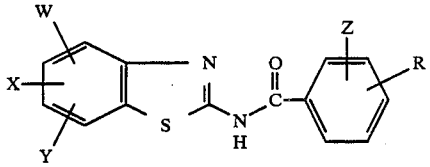

I and

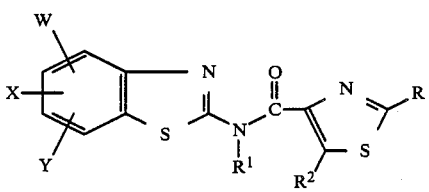

II

-continued and

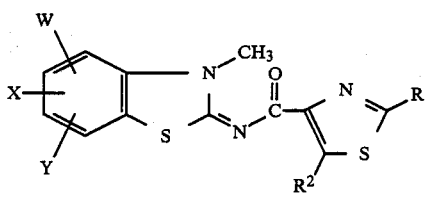

and

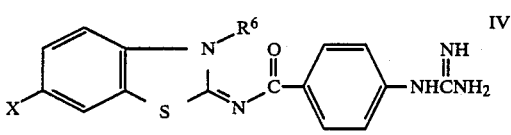

or a pharmaceutically acceptable salt thereof, wherein X is $(C_1-C_5)$alkyl, hydrogen, $(C_1-C_5)$alkoxy, $(C_1-C_5)$alkylthio, $(C_1-C_5)$alkylsulfinyl, $(C_1-C_5)$alkylsulfonyl, flouro, chloro, bromo, nitro, trifluoromethyl, carbamyl, N,N-di$(C_1-C_3)$alkylcarbamyl, phenyl, fluorophenyl, methoxyphenyl, hydroxyphenyl, cyano, cyclohexyl or hydroxy $(C_1-C_5)$alkyl; Y is hydrogen, $(C_1-C_5)$alkyl, $(C_1-C_5)$alkoxy, fluoro or chloro; W is hydrogen, $(C_1-C_5)$alkoxy, $(C_1-C_5)$alkyl, cyano, fluoro, chloro or bromo; X and Y when taken together form a benzo ring or a tetrahydrobenzo ring; Z is hydrogen, fluoro, chloro, bromo or $(C_1-C_3)$alkyl; R is a substituent of the formula

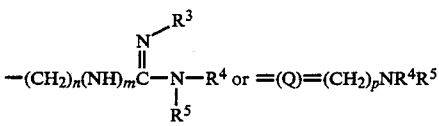

where m is an integer of 0 to 1; n is an integer of 0 to 2; $R^3$, $R^4$ and $R^5$ are each hydrogen or $(C_1-C_3)$alkyl; Q is $CH_2$, O, $NR^4$ or S; p is an integer of 0 to 3; $R^4$ and $R^5$ when taken together with the nitrogen to which they are attached are piperidino, pyrrolidino, morpholino, thiomorpholino, piperazino or 4-$(C_1-C_5)$alkylpiperazino; $R^1$ is hydrogen or methyl; $R^2$ is hydrogen, $(C_1-C_4)$alkyl, nitro, cyano, trifluoromethyl, fluoro, chloro or bromo; and $R^6$ is $(C_1-C_3)$alkyl, $(C_1-C_3)$alkoxycarbonylmethyl or benzyloxycarbonylmethyl, with the proviso that in compounds of formula I, R is at the m or p-position to the carbonyl attachment and when Q is O, $NR^4$ or S, p is 2 to 3.

2. A compound of claim 1, formula II.
3. A compound of claim 2, wherein R is

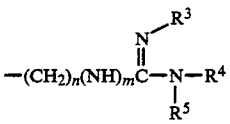

where n is 0, m is 1, $R^3$, $R^4$ and $R^5$ are each hydrogen, W is hydrogen, $R^1$ is hydrogen and $R^2$ is hydrogen, $(C_1-C_4)$alkyl or bromo.

4. The compound of claim 3, wherein X is 6-trifluoromethyl and Y and $R^2$ are each hydrogen.
5. The compound of claim 3, wherein X is 5-fluoro, Y is hydrogen and $R^2$ is i-propyl.

6. The compound of claim 3, wherein X and Y taken together are 4,5-benzo and $R^2$ is hydrogen.
7. The compound of claim 3, wherein X is 4-methoxy, Y is hydrogen and $R^2$ is ethyl.
8. The compound of claim 3, wherein X is 5-fluoro, Y is hydrogen and $R^2$ is methyl.
9. The compound of claim 3, wherein X is 5-fluoro, Y is 7-fluoro and $R^2$ is ethyl.
10. The compound of claim 3, wherein X is 4-fluoro, Y is 7-methyl and $R^2$ is ethyl.
11. The compound of claim 3, wherein X is 6-cyano, Y is hydrogen and $R^2$ is methyl.
12. The compound of claim 3, wherein X is 5-fluoro and Y and $R^2$ are each hydrogen.
13. The compound of claim 3, wherein X is 5-chloro, Y is hydrogen and $R^2$ is methyl.
14. The compound of claim 3, wherein X is 5-fluoro, Y is hydrogen and $R^2$ is ethyl.
15. The compound of claim 3, wherein X is 6-phenyl and Y and $R^2$ are each hydrogen.
16. The compound of claim 3, wherein X is 5-fluoro, Y is 6-fluoro and $R^2$ is hydrogen.
17. The compound of claim 3, wherein X is 4-methyl, Y is 5-chloro and $R^2$ is hydrogen.
18. The compound of claim 3, wherein X is 5-fluoro, Y is 6-bromo and $R^2$ is hydrogen.
19. The compound of claim 3, wherein X is 5-fluoro, Y is hydrogen and $R^2$ is bromo.
20. The compound of claim 3, wherein X is 5-chloro, Y is 6-methyl and $R^2$ is hydrogen.
21. The compound of claim 3, wherein X is 7-trifluoromethyl, Y is 6-chloro and $R^2$ is hydrogen.
22. The compound of claim 3, wherein X is 6-phenyl, Y is 4-methoxy and $R^2$ is hydrogen.
23. A compound of claim 2, wherein R is

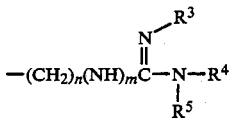

where n is 0, m is 1, $R^3$, $R^4$ and $R^5$ are each hydrogen, $R^1$ is hydrogen and $R^2$ is $(C_1-C_4)$alkyl.

24. The compound of claim 23, wherein X is 7-fluoro, Y is 5-fluoro, W is 4-methoxy and $R^2$ is ethyl.
25. A compound of claim 2, wherein R is

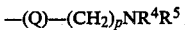

where p is 2, $R^4$ and $R^5$ are each hydrogen or $(C_1-C_3)$alkyl and $R^1$ and $R^2$ are each hydrogen.

26. The compound of claim 25, wherein Q is S, $R^4$ and $R^5$ are each hydrogen, X is 6-phenyl and Y and W are each hydrogen.
27. The compound of claim 25, wherein Q is NH, $R^4$ and $R^5$ are each methyl, X is 6-phenyl and Y and W are each hydrogen.
28. The compound of claim 25, wherein Q is NH, $R^4$ and $R^5$ are each methyl, X is 6-cyano and Y and W are each hydrogen.
29. The compound of claim 25, wherein Q is S, $R^4$ and $R^5$ are each hydrogen, X is 5-fluoro and Y and W are each hydrogen.
30. A compound of claim 1, formula I.
31. A compound of claim 30, wherein Z is hydrogen and R is

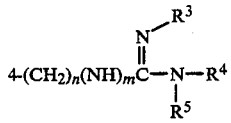

where n is 0, m is 1 and $R^3$, $R^4$ and $R^5$ are each hydrogen.

32. The compound of claim 31, wherein X is 6-nitro and Y and W are each hydrogen.

33. The compound of claim 31, wherein X is 5-fluoro, Y is 6-fluoro and W is hydrogen.

34. A compound of claim 2, wherein R is

—(Q)—$(CH_2)_p NR^4 R^5$ where $R^4$ and $R^5$ are each hydrogen or $(C_1-C_3)$alkyl or together with the nitrogen to which they are attached is piperidino; $R^1$ and W are each hydrogen and $R^2$ is hydrogen or $(C_1-C_4)$alkyl.

35. The compound of claim 34, wherein X is 5-chloro, Y is 6-chloro, $R^2$ is ethyl, Q is NH, p is 2 and $R^4$ and $R^5$ are each methyl.

36. The compound of claim 34, wherein X is 5-chloro, Y is 6-chloro, $R^2$ is ethyl, Q is NH, p is 3 and $R^4$ and $R^5$ are each methyl.

37. The compound of claim 34, wherein X is 6-cyano, Y is hydrogen, $R^2$ is ethyl, Q is NH, p is 3 and $R^4$ and $R^5$ are each methyl.

38. The compound of claim 34, wherein X is 6-cyano, Y is hydrogen, $R^2$ is ethyl, Q is NH, p is 2 and $R^4$ and $R^5$ together with the nitrogen to which they are attached is piperidino.

39. The compound of claim 34, wherein X is 6-n-butyl, Y is hydrogen, $R^2$ is hydrogen, Q is $CH_2$, p is 0 and $R^4$ and $R^5$ are each hydrogen.

* * * * *